United States Patent
Kakuda et al.

(10) Patent No.: US 6,570,042 B2
(45) Date of Patent: *May 27, 2003

(54) PRODUCTION OF ADAMANTANEDIOLS

(75) Inventors: Minoru Kakuda, Chiba (JP); Takashi Onozawa, Mie (JP); Hiroshi Kurata, Ibaraki (JP); Kikuo Furukawa, Ibaraki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/955,077

(22) Filed: Sep. 19, 2001

(65) Prior Publication Data

US 2002/0040170 A1 Apr. 4, 2002

(30) Foreign Application Priority Data

Sep. 22, 2000  (JP) ........................................ 2000-289427

(51) Int. Cl.$^7$ .............................................. C07C 35/22
(52) U.S. Cl. ....................................................... 568/818
(58) Field of Search ......................................... 568/818

(56) References Cited

U.S. PATENT DOCUMENTS 6,187,967 B1 * 2/2001 Kakuda

FOREIGN PATENT DOCUMENTS

| EP | 1 026 140 A1 | | 8/2000 |
|----|--------------|---|--------|
| EP | 1026140 A | * | 8/2000 |
| JP | 2000-219646 | | 8/2000 |

OTHER PUBLICATIONS

Mario Bressan and Antonino Morvillo, "Selective Oxidation of Alkanes and Ethers mediated by Ruthenium (II) Complexes", J. Chem. Soc., Chem. Commun., 1989, pp. 421–423 (XP–002137291).

* cited by examiner

Primary Examiner—Michael L. Shippen
(74) Attorney, Agent, or Firm—Oblon, Spivak, McClelland, Maier & Neustadt, P.C.

(57) ABSTRACT

Adamantanediols are produced by the hydroxylation of adamantane compounds in a water/organic solvent two-phase system in the presence of a ruthenium compound and a hypochlorite. Throughout the hydroxylation, the hypochlorite concentration in the water phase is regulated within a narrow limited range, for example, by monitoring the pH of the reaction system. With such a control of the hypochlorite concentration, the adamantanediols are produced in a high selectivity and a high yield.

8 Claims, No Drawings

PRODUCTION OF ADAMANTANEDIOLS

BACKGROUND OF THE INVENTION

1. Field of the Invention

The present invention relates to a process of producing adamantanediols useful as raw materials for high performance polymers, synthetic lubricants and plasticizers, and as intermediates for preparing organic chemicals such as pharmaceutical compounds and agricultural compounds.

2. Description of the Prior Art

The inventors have proposed in Japanese Patent Application Laid-Open No. 2000-219646 (U.S. Pat. No. 6,187,967) a method for producing adamantanols by the hydroxylation of adamantane compounds in a water/organic solvent two-phase system by hypochlorous acid or its salt in the presence of a ruthenium compound catalyst. In the proposed method, the hydroxylation is carried out by adding hypochlorous acid or its salt dropwise with the pH of the reaction system maintained at 0.1 to 11, and the adamantanediols are selectively produced in high yields. However, since the optimum pH for the hydroxylation largely depends on the chemical composition of the reaction system, the proposed method is still insufficient because of difficulty in controlling the hydroxylation.

SUMMARY OF THE INVENTION

An object of the present invention is to provide a method for producing adamantanediols in a high selectivity and a high yield by optimizing the conditions for the hydroxylation more accurately and easily.

The inventors have examined in more detail the production of the adamantanediols by the hydroxylation of an adamantane compound with a hypochlorite in the presence of a ruthenium compound catalyst in a water/organic solvent two-phase system. As a result thereof, the inventors have found that the adamantanediols are selectively produced in high yields by carrying out the hydroxylation with the concentration of the hypochlorite in the water phase maintained within the range of 0.001 to 2.0 mmol/g. The inventors have further found that the adamantanediols are produced more efficiently by regulating the variation of the hypochlorite concentration within 0.1 mmol/g or less. The present invention has been accomplished on the basis of these findings.

Thus, the present invention provides a method for producing an adamantanediol, which comprises a step of hydroxylating an adamantane compound in a water/organic solvent two-phase system in the presence of a ruthenium compound and a hypochlorite while regulating the concentration of the hypochlorite in the water phase within a limited range throughout the hydroxylation.

DETAILED DESCRIPTION OF THE INVENTION

The adamantane compound used in the present invention as the starting material is represented by the following formula:

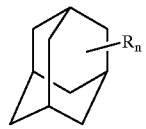

wherein R or a plurality of R groups are independently alkyl group, aryl group, cycloalkyl group, alkoxyl group, aryloxy group, acyloxy group or halogen, and "n" is an integer from 0 to 14 with the proviso that at least two bridge-head carbon atoms are not substituted by R.

In the above formula, the alkyl group may be $C_1$–$C_{10}$ alkyl such as methyl, ethyl, propyl, butyl and hexyl, preferably $C_1$–$C_6$ alkyl and more preferably $C_1$–$C_4$ alkyl. The aryl group may be phenyl and naphthyl, and the cycloalkyl may be cyclohexyl or cyclooctyl. The alkoxyl group may be $C_1$–$C_{10}$ alkoxyl such as methoxyl, ethoxyl, propoxyl, butoxyl and hexyloxy. The aryloxy group may be phenoxyl. The acyloxy group may be $C_2$–$C_6$ acyloxy such as acetyloxy, propionyloxy and butyryloxy. The halogen may be chlorine, bromine and iodine.

The adamantanediols referred to in the present invention may include 1,3-adamantanediol, 1,2-adamantanediol, and 1,4-adamantanediol, which may be substituted by R in the above formula.

In the present invention, the adamantane compound is hydroxylated by a high-oxidation state ruthenium(VI to VIII) compound generated by the reaction between the ruthenium compound and the hypochlorite. The ruthenium compound usable in the present invention may include metallic ruthenium, ruthenium(IV) dioxide, ruthenium(VIII) tetraoxide, ruthenium(III) hydroxide, ruthenium(III) chloride, ruthenium(III) bromide, ruthenium(III) iodide, ruthenium(IV) sulfate, and hydrates of the above ruthenium compounds. The ruthenium compounds may be used alone or in combination of two or more. The ruthenium compound is used in an amount of preferably 0.001 to 2.0 mol, more preferably 0.05 to 0.4 mol per one mol of the adamantane compound. An amount less than the above range decreases the reaction rate, and an amount more than the above range results in the excessive use of the expensive ruthenium compound, each being undesirable for industrial process.

The hypochlorite may include sodium hypochlorite, lithium hypochlorite, potassium hypochlorite and calcium hypochlorite with sodium hypochlorite being preferred, which is added to the reaction system as an aqueous solution of 6 to 35% by weight. When the concentration of the hypochlorite is lower than 6% by weight, the extraction efficiency of the adamantanediols from the water phase is poor and a labor-intensive disposal of waste liquids are required because of a large amount of water phase. When higher than 35% by weight, the side reactions are likely to occur to reduce the yield of the adamantanediols.

In the method of the present invention, the hypochlorite is used in an amount of 1.5 to 4.0 mol, preferably 2.0 to 3.0 mol per one mol of the adamantane compound. When the addition amount is less than 1.5 mol, a large amount of the adamantane compound remains unreacted and a large amount of adamantanemonols is by-produced, thereby resulting in a low selectivity to the adamantanediols. When larger than 4.0 mol, a large amount of adamantanetriols is by-produced to reduce the selectivity to the adamantanediols.

In the present invention, to achieve a high selectivity to or a high yield of the adamantanediols, it is important to regulate the hypochlorite concentration in the water phase within a narrow limited range throughout the hydroxylation. Namely, the concentration of the hypochlorite in the water phase is preferably controlled within the range of 0.001 to 0.5 mmol/g, more preferably 0.001 to 0.2 mmol/g. If the concentration exceeds 0.5 mmol/g, the side reactions such as chlorination occur, thereby failing to produce the adamantanediols in good yields. If the concentration is less than 0.001 mmol/g, the hypochlorite added to the reaction system is readily decomposed to reduce the reaction efficiency. The variation of the hypochlorite concentration in the water phase is preferably regulated within 0.1 mmol/g or less.

The concentration of the hypochlorite in the water phase may be directly measured. If the direct measurement is difficult, the concentration may be indirectly controlled by measuring and controlling an indicative of the concentration of the hypochlorite, such as hydrogen ion concentration, oxidation-reduction potential, and absorbance.

For example, the concentration of the hypochlorite is controlled by the following methods.

(1) A hypochlorite solution and an acid solution are added to the reaction system in appropriate amounts for maintaining the pH within a limited range through a metering pump for hypochlorite supply and a metering pump for acid supply, each being connected to a pH controller.

(2) A hypochlorite solution is added to the reaction system in appropriate amount for maintaining the potential constant through a metering pump for hypochlorite supply which is connected to an oxidation-reduction potential controller.

(3) The hypochlorite consumption per unit time is calculated from the reaction rate measured in advance. The hypochlorite solution is added from a metering pump in an amount so as to make up for the consumed hypochlorite.

The control of the hypochlorite concentration by pH utilizes the phenomenon that the pH of the reaction system decreases with increasing consumption of the hypochlorite accompanied with the progress of the hydroxylation, and the hypochlorite is added to the reaction system when the pH becomes lower than the set value, thereby controlling the hypochlorite concentration in the water phase within a limited range. Since free alkali possibly contained in the hypochlorite raises the pH, the set value of the pH should be occasionally adjusted or an acid should be added in an amount equivalent to the free alkali.

The hydroxylation is carried out at pH of 2.5 to 10, preferably at pH of 3 to 8. A pH exceeding 10 is disadvantageous because perruthenate ion having a low catalytic activity is generated. When the pH is lower than 2.5, chlorine gas is evolved to adversely affect the hydroxylation. By regulating the pH variation within ±2.0, preferably within ±0.5 in the pH range of 2.5 to 10, the hypochlorite concentration in the water phase and its variation are regulated within the limited ranges described above. More preferably, the pH at the beginning of the hydroxylation is regulated within the limited range.

The acid for controlling the pH of the reaction system may include a water-soluble organic acid such as formic acid, acetic acid and propionic acid, and a water-soluble inorganic acid such as hydrochloric acid, sulfuric acid, nitric acid and phosphoric acid, with the inorganic acid being preferred in view of easy purification of the product and hydrochloric acid being more preferred because the reaction is less affected adversely. The concentration of the acid solution is preferably 0.1 to 50% by weight, more preferably 0.5 to 10% by weight in view of easy control of the pH.

The organic solvent usable in the present invention may be selected from solvents which are less compatible with water, capable of well dissolving the high-oxidation state ruthenium compound and inert to the hydroxylation. If highly compatible with water, the recovery of the organic solvent becomes costly, and the hydroxylation proceeds slowly if the organic solvent is poor in dissolving the high-oxidation state ruthenium compound. Examples of the organic solvent are alkyl halides such as dichloromethane, 1,2-dichloroethane, chloroform, carbon tetrachloride, 1,1,2-trichloroethane, 1,4-dichlorobutane, and 1,6-dichlorohexane; esters such as methyl acetate, ethyl acetate, and isopropyl acetate; aryl halides such as hexachlorobenzene and 1,1,1-trifluorotoluene; and hydrocarbons such as hexane, heptane and octane. Of the above organic solvents, preferred are 1,2-dichloroethane and ethyl acetate. The above organic solvent may be used alone or in combination of two or more. The amount of the solvent to be used is 0.1 to 20 parts by weight, preferably 1 to 10 parts by weight per one part by weight of the starting adamantane compound. The charge ratio of water and the organic solvent is preferably 1:2 to 1:20 by weight.

The reaction temperature is 10 to 100° C., preferably 40 to 70° C. A reaction temperature lower than the above range extremely lowers the reaction rate. When the reaction temperature is higher than the above range, the selectivity is decreased because of the decomposition of hypochlorite and the increased side reactions. The reaction time is preferably 100 to 500 minutes. The hydroxylation may be carried out in any of known reaction apparatus equipped with a stirring device.

After transferring the ruthenium compound into the water phase by the addition of alkali, the reaction product mixture is extracted with an alcohol having 4 to 8 carbon atoms, thereby separating the ruthenium compound into the water phase and the adamantanediols into the organic phase, from which the adamantanediols are isolated by a known method such as filtration, concentration, distillation, crystallization and recrystallization. The alkali usable may include metal hydroxides such as sodium hydroxide, potassium hydroxide, lithium hydroxide and barium hydroxide; and tetralkylammonium hydroxides such as tetramethylammonium hydroxide, tetraethylammonium hydroxide, tetrapropylammonium hydroxide and tetrabutylammonium hydroxide. Preferred are sodium hydroxide and potassium hydroxide. Alkali may be added directly or added in the form of aqueous solution. The alcohol for extraction may include 1-butanol, 2-butanol, 2-methyl-1-propanol, 1-pentanol, 3-pentanol, 3-methyl-1-butanol, 2-methyl-2-butanol, 1-hexanol, 4-methyl-2-pentanol, 2-ethyl-1-butanol, cyclohexanol, 1-heptanol, 1-octanol and benzyl alcohol. Of the above alcohols, preferred are 1-butanol, 1-pentanol, 1-hexanol, 2-butanol, 2-methyl-1-propanol, 3-methyl-1-butanol and benzyl alcohol.

The ruthenium compound is reduced in the water phase to precipitate as black insolubles which are recovered by filtration and reused in the next run of reaction.

The present invention will be described in further detail by way of the following Examples. However, it should be construed that the following examples are merely illustrative and not intended to limit the invention thereto.

EXAMPLE 1

Into a 10-L five-necked jacketed flask equipped with a stirring device, a thermometer, a Dimroth condenser and a pH electrode, were charged 408 g (3 mol) of adamantane, 3000 mL of ethyl acetate, 20 g of ruthenium chloride n-hydrate (corresponding to 82 mmol of dihydrate) and 500 g of water. After heating to 46° C, the pH was adjusted to 4. Then, a 12% aqueous solution of sodium hypochlorite was started to be added dropwise. The dropping speed was regulated so as to add 4120 g (7.5 mol) of the aqueous solution of sodium hypochlorite over 400 min as calculated from the reaction rate previously measured. The content of the free alkali in the aqueous solution of sodium hypochlorite was 0.5%. The reaction was continued by maintaining the pH of the reaction system at 4.0 to 4.5 by adding a 5% hydrochloric acid in an amount equivalent to the free alkali in the aqueous solution of sodium hypochlorite. During the reaction, the hypochlorite concentration in the water phase varied between 0.03 and 0.09 mmol/g.

After the addition of the sodium hypochlorite was completed, 80 g of a 25 wt % NaOH aqueous solution and 3000 mL of hexanol were added to separate the reaction mixture into the organic phase and the water phase. The gas chromatographic analysis on each phase showed that the conversion of adamantane was 100%, the yield of 1-adanantanol was 9%, the yield of 1,3-adamantanediol was 70%, and the yield of 1,3,5-adamantanetriol was 14%. The ruthenium catalyst was recovered as black precipitates by filtering the water phase.

EXAMPLE 2

The procedure of Example 1 was repeated except for omitting the addition of hydrochloric acid. The hypochlorite concentration in the water phase varied between 0.028 and 0.097 mmol/g, and the pH varied between 4.0 and 7.4. The gas chromatographic analysis showed that the conversion of adamantane was 100%, the yield of 1-adanantanol was 6%, the yield of 1,3-adamantanediol was 61%, and the yield of 1,3,5-adamantanetriol was 12%.

EXAMPLE 3

The procedure of Example 1 was repeated except for dropping the aqueous solution of sodium hypochlorite in a different manner. The aqueous solution of sodium hypochlorite and hydrochloric acid were added dropwise from a metering pump for sodium hypochlorite supply and a metering pump for hydrochloric acid supply both being connected to a pH controller in a dropping speed so as to maintain the pH at 4 until the aqueous solution of sodium hypochlorite was added 4344 g (7.5 mmol) in total. The hypochlorite concentration in the water phase varied between 0.015 and 0.080 mmol/g. After the reaction was completed, 54 g of a 25 wt % NaOH aqueous solution and 3000 mL of hexanol were added to separate the reaction product mixture into the water phase and the organic phase. The gas chromatographic analysis showed that the conversion of adamantane was 100%, the yield of 1-adanantanol was 5%, the yield of 1,3-adamantanediol was 70%, and the yield of 1,3,5-adamantanetriol was 14%.

EXAMPLE 4

The procedure of Example 3 was repeated except for maintaining the pH at 6 to 6.5. The hypochlorite concentration in the water phase varied between 0.0040 and 0.024 mmol/g. The gas chromatographic analysis showed that the conversion of adamantane was 100%, the yield of 1-adanantanol was 9%, the yield of 1,3-adamantanediol was 65%, and the yield of 1,3,5-adamantanetriol was 13%.

EXAMPLE 5

The procedure of Example 3 was repeated except for maintaining the pH at 8 to 8.5. The hypochlorite concentration in the water phase varied between 0.019 and 0.088 mmol/g. The gas chromatographic analysis showed that the conversion of adamantane was 100%, the yield of 1-adanantanol was 25%, the yield of 1,3-adamantanediol was 52%, and the yield of 1,3,5-adamantanetriol was 9%.

COMPARATIVE EXAMPLE 1

The procedure of Example 1 was repeated except for adding dropwise 4259 g (7.5 mol) of the aqueous solution of sodium hypochlorite over 36 min at a constant speed. To maintain the pH at 8 to 8.5, hydrochloric acid was added. The hypochlorite concentration in the water phase varied between 0.55 and 0.67 mmol/g. The gas chromatographic analysis showed that the conversion of adamantane was 75%, the yield of 1-adanantanol was 25%, the yield of 1,3-adamantanediol was 4%, and the yield of 1,3,5-adamantanetriol was 0.3%.

As described above, by controlling the addition of the hypochlorite so that the variation of the hypochlorite concentration in the water phase may be regulated within a limited range, the hydroxylation of the adamantane compound is optimized more accurately to produce the adamantanediols in a high selectivity (70% or more) and a high yield (70% or more).

What is claimed is:

1. A method for producing an adamantanediol, the method comprising hydroxylating an adamantane compound in a water/organic solvent two-phase system in the presence of a ruthenium compound and a hypochiorite while regulating the concentration of the hypochlorite in the water phase within a limited range throughout the hydroxylation, wherein the concentration of the hypochlorite in the water phase is 0.001 to 0.2 mmol/g, the variation of the concentration of the hypochlorite in the water phase is regulated to 0.1 mmol/g or less, and the hydroxylation is carried out at a pH of 2.5 to 7.4.

2. The method according to claim 1, wherein the adamantane compound is represented by the following formula:

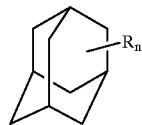

wherein $R_n$ represents n groups independently selected from the group consisting of an alkyl group, an aryl group, an cycloalkyl group, an aryloxy group, an acyloxy group and a halogen atom, and n is an integer from 0 to 14, with the proviso that at least two bridge-head carbon atoms are not substituted by R.

3. The method according to claim 1, wherein the variation of the pH of the water phase is regulated in a limited range.

4. The method according to claim 3, wherein the pH of the water phase is a pH at the beginning of the hydroxylation.

5. The method according to claim 3, wherein the variation of the pH is regulated with in ±2.0.

6. A method for producing an adamantanediol, the method comprising hydroxylating an adamantane compound in a water/organic solvent two-phase system in the presence of a ruthenium compound and a hypochlorite while regulating the concentration of the hypochlorite in the water phase within a limited range throughout the hydroxylation, wherein the concentration of the hypochlorite in the water phase is 0.001 to 0.5 mmol/g, the variation of the concentration of the hypochlorite in the water phase is regulated to 0.1 mmol/g or less, and the hydroxylation is carried out at apH of 2.5 to 7.4.

7. The method according to claim 1, further comprising producing 1,3-adamantanediol with a yield of 61% or more.

8. The method according to claim 6, further comprising producing 1,3-adamantanediol with a yield of 61% or more.

* * * * *